United States Patent [19]

Mar

[11] Patent Number: 5,488,768
[45] Date of Patent: Feb. 6, 1996

[54] METHOD OF FORMING A DEFIBRILLATION ELECTRODE CONNECTION

[75] Inventor: Craig E. Mar, Fremont, Calif.

[73] Assignee: Ventritex, Inc., Sunnyvale, Calif.

[21] Appl. No.: 126,291

[22] Filed: Sep. 24, 1993

[51] Int. Cl.⁶ .............................. H01R 43/02; H01R 43/04
[52] U.S. Cl. ...................... 29/860; 29/DIG. 48; 128/642; 228/173.5; 228/180.5; 228/904; 607/122
[58] Field of Search ............................ 29/621, 860, 861, 29/DIG. 48; 148/103, 437; 128/642; 228/55, 180.5, 173.5, 904; 607/122, 125, 126, 4; 439/66, 700, 824

[56] References Cited

U.S. PATENT DOCUMENTS

| | | | |
|---|---|---|---|
| 3,335,389 | 8/1967 | Reichardt | 439/700 X |
| 3,917,148 | 11/1975 | Runyon | 228/55 X |
| 3,942,536 | 3/1976 | Mirowski et al. | 607/17 |
| 4,161,952 | 7/1979 | Kinney et al. | 607/122 |
| 4,164,067 | 8/1979 | Brandt et al. | 29/621 X |
| 4,214,804 | 7/1980 | Little | 439/669 X |
| 4,314,095 | 2/1982 | Moore et al. | 128/642 X |
| 4,328,812 | 5/1982 | Ufford et al. | 607/122 |
| 4,495,917 | 1/1985 | Byers | 607/61 X |
| 4,662,382 | 5/1987 | Sluetz et al. | 607/126 |
| 4,715,891 | 12/1987 | Ovshinsky et al. | 148/103 X |
| 4,747,889 | 5/1988 | Nishio et al. | 148/437 |
| 4,784,161 | 11/1988 | Skalsky et al. | 607/122 X |
| 4,827,932 | 5/1989 | Ideker et al. | 128/642 X |
| 4,860,769 | 8/1989 | Fogarty et al. | 607/119 |
| 4,922,927 | 5/1990 | Fine et al. | 607/122 |
| 4,998,975 | 3/1991 | Cohen et al. | 607/2 |
| 5,007,422 | 4/1991 | Pless et al. | 607/4 |
| 5,007,436 | 4/1991 | Smits | 607/125 |
| 5,016,808 | 5/1991 | Heil, Jr. et al. | 228/176 |
| 5,025,554 | 6/1991 | Dohi | 29/860 |
| 5,052,407 | 10/1991 | Hauser et al. | 607/125 |
| 5,144,960 | 9/1992 | Mehra et al. | 607/125 |
| 5,167,512 | 12/1992 | Walkup | 439/66 |
| 5,174,288 | 12/1992 | Bardy et al. | 607/2 |
| 5,226,260 | 7/1993 | Mar et al. | 451/39 |

FOREIGN PATENT DOCUMENTS

| | | | |
|---|---|---|---|
| 1119742 | 6/1956 | France | 439/824 |
| 186702 | 9/1956 | Germany | 439/824 |

OTHER PUBLICATIONS

"A Subcutaneous Lead Array for Implantable Cardioverter Defibrillators", Jordaens, et al, PACE, vol. 16, Part I (Jul. 1993).

Bresg "Spring Contator" IBM Tech. Discl. Bulletin, vol. 10, No. 4, Sep. 1967 p. 363.

Barkhuff "Connector" IBM Tech. Discl. Bulletin, vol. 22, No. 1, Jun. 1979, pp. 158–159.

*Primary Examiner*—Peter Vo
*Attorney, Agent, or Firm*—Steven M. Mitchell; M. Elizabeth Bush; Mark J. Meltzer

[57] ABSTRACT

A method for electrically attaching electrode wire to a conductor in a defibrillation lead is disclosed. The method comprises melting the end of the wire with a hydrogen torch to form a ball of metal, then crimping or welding the ball to the conductor or to a joining piece attached to the conductor. Also, a hydrogen torch (water welder) may be used to join two or more electrode wires to each other.

12 Claims, 8 Drawing Sheets

METHOD OF FORMING A DEFIBRILLATION ELECTRODE CONNECTION

FIELD OF THE INVENTION

This invention relates to medical electrical stimulation electrodes in general and to implantable defibrillation electrodes in particular.

BACKGROUND OF THE INVENTION

It is well known that cardiac arrhythmias such as ventricular fibrillation may be controlled with devices such as implantable defibrillators. Many different types of defibrillation electrodes have been suggested over the years, as can be seen from the following examples. In this discussion, no distinction will be made between cardioversion and defibrillation; both will be referred to as defibrillation.

U.S. Pat. No. 3,942,536 issued to Mirowski et al. discloses an intravascular bipolar catheter electrode system wherein each of two electrodes is composed of a plurality of spaced, low impedance rings. As implanted, the first electrode is located within the right ventricle (RV) and the second electrode is located in the superior vena cava (SVC).

In U.S. Pat. No. 4,161,952 issued to Kinney et al., a catheter electrode has a coil of wound spring wire, with filler material beneath and between individual turns of coil such that only the outside of the wound wire is exposed to the patient's body. It is designed to reside in or about the heart, as in the SVC or in the coronary sinus (CS).

U.S. Pat. No. 4,922,927 issued to Fine et al. teaches the use of tightly wound wire forming a tight coil on a support that is flared to provide a greater diameter along its midsection than at its ends, to form an RV electrode. A copper-zirconium alloy wrapped with tantalum and coated with iridium oxide is suggested for the tightly wound wire.

Other types of transvenously placed leads are disclosed in U.S. Pat. No. 4,998,975 issued to Cohen et al. One lead is placed through the heart wall, and into the pericardial space, and another is placed endocardially in a conventional manner. Both leads are shown with several embodiments, with the examples of general electrode construction being to expose a section of the conductor coil, or to use ring electrodes similar to those used in conventional bipolar pacemaker leads. Cohen et al. also describe two methods for steering more current to a selected region of the heart. The first method is to apply various voltages to the connectors of each of four electrodes. The second method uses the resistance of conductors, both between connector and electrode, and between two electrodes on the same lead, and the body tissue resistance between electrodes on different leads, to form a voltage divider, thus creating a different potential at each electrode.

Another lead system patent, U.S. Pat. No. 5,007,436 issued to Smits, describes electrodes of both J and straight configurations, for use in the RV, right atrium, great cardiac vein, or CS. The fabrication methods suggested use close wound conductive coils mounted exterior to an elongated insulative sheath, or the method of Kinney et al.

Spiral shaped electrodes for endocardial, epicardial, or extrapericardial implantation are described in Heil, Jr. et al., U.S. Pat. No. 5,016,808, Fogarty et al., U.S. Pat. No. 4,860,769, and Hauser et al., U.S. Pat. No. 5,052,407. The electrodes of these patents use various construction techniques, including electrodeposition or vapor deposition onto a plastic tube, helically wound wire (round or ribbon, unifilar or multifilar, single or double helix) or conductive rings on a flexible insulating portion, and conductive screen wrapped around a tubular body.

Other defibrillation leads are disclosed in Mehra et al., U.S. Pat. No. 5,144,960, and in Bardy et al., U.S. Pat. No. 5,174,288.

Endotak SQ Model 0048 (Cardiac Pacemakers Inc., St. Paul, Minn., USA), described in "A Subcutaneous Lead Array for Implantable Cardioverter Defibrillators" by Jordaens et al., published in PACE, Vol. 16, Jul. 1993, Part I, is an electrode system consisting of three conductive elements that can be subcutaneously inserted. The conductive elements of this "array lead" are made of electrically common multifilar coil, joined in a silicone yoke, and separately introduced with a lead tunneler and peel-away sheaths.

Epicardial defibrillation leads typically are made of wire mesh, which is welded in several places to another piece of mesh or foil, which is in turn crimped to a conductor. The mesh wire diameter is typically 0.10 min. The epicardial lead shown in Moore et al., U.S. Pat. No. 4,314,095, has an electrode connection formed by crimping a piece of wire mesh and a conductor into the channel of a U-shaped clip, then welding the mesh portion to a wire mesh electrode. Ideker et al., in U.S. Pat. No. 4,827,932, disclose a connection formed by spot welding a pair of tabs to both sides of a mesh electrode, then inserting the ends of the tabs and a coil conductor into a sleeve, then crimping the components together.

Endocardial lead electrodes for pacing and defibrillation typically are joined to conductors by crimps or welds. U.S. Pat. No. 4,662,382, issued to Sleutz et al., describes such a connection made by crimping an electrode wire and a conductor wire into a sleeve. A second electrode has a hollow portion to accept a conductor coil and crimp pin, which get crimped together. U.S. Pat. No. 4,784,161, issued to Skalsky et al., describes a crimp connection having both an electrode wire and conductor wires wrapped around a shaft, with a crimp sleeve over both. In another embodiment, a bundle of electrode wires and a helical conductor have a support pin through the middle of them; a crimp sleeve covers both the conductor and the bundled wires. U.S. Pat. Nos. 4,214,804 and 4,328, 812, to Little and Ufford et al. respectively, disclose press fit, or swage fit, connections of ring electrodes to conductor coils. U.S. Pat. No. 4,161,952, to Kinney et al., teaches the use of metal connecting pieces to which is welded a 0.76 mm diameter electrode wire. An electrically conductive polymer such as silver-filled epoxy is used to electrically connect the conductor to the metal connecting pieces.

As defibrillator technology improves and the demand for defibrillators increases, it becomes increasingly desirable to have leads available that are easily implanted and capable of withstanding repeated flexing over a long period of time. In order to provide improved flexibility, prior art systems have begun to use very small wires which are fatigue resistant. This however presents a problem of making reliable electrical connections. Crimps, swages, press fit connections, and the like require at least some deformation of the parts being connected, In the case of fine wires, say 0.08 mm diameter, it is very difficult to deform the wire to form a strong connection without weakening or breaking it. This is especially true considering that tolerances on crimp sleeves, crimp pins, and crimp tool jaws can easily add up to more than the diameter of the wire being crimped. Welds require some melting of the material being welded. Resistance welds in particular require the application of pressure. For fine wire, the wire may melt through or be crushed during the welding process. For fine coiled wire, neither crimping nor simple welding is suitable because the wire needs to be unwound before pressure is applied, since flattening a fine coil will break it. On the other hand, the coiled wire could become damaged by the process of unwinding it. Therefore, another method must be used to join these small wire electrode elements to their lead conductors.

SUMMARY OF THE INVENTION

The present invention provides an electrode connection for a lead for use with an implantable defibrillator system. In the preferred embodiment, small coils made of fine platinum iridium wire serve as the electrode material. These fine wire electrodes are attached to the rest of the lead by melting their ends into balls of metal with a hydrogen torch, and welding the balls to a sleeve to which a conductor is attached.

In an alternative embodiment, the connection is made by melting the small electrode coils into one large ball, then crimping the ball into a sleeve to which a conductor is attached.

In a third embodiment, the ends of two or more electrode coils are joined together by using a hydrogen torch to melt them into a ball, It is thus an object of the present invention to provide an electrical connection for wire electrodes for an implantable defibrillator.

It is another object of the invention to provide an electrode connection that is easily manufactured.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION OF THE INVENTION

Figure 1:
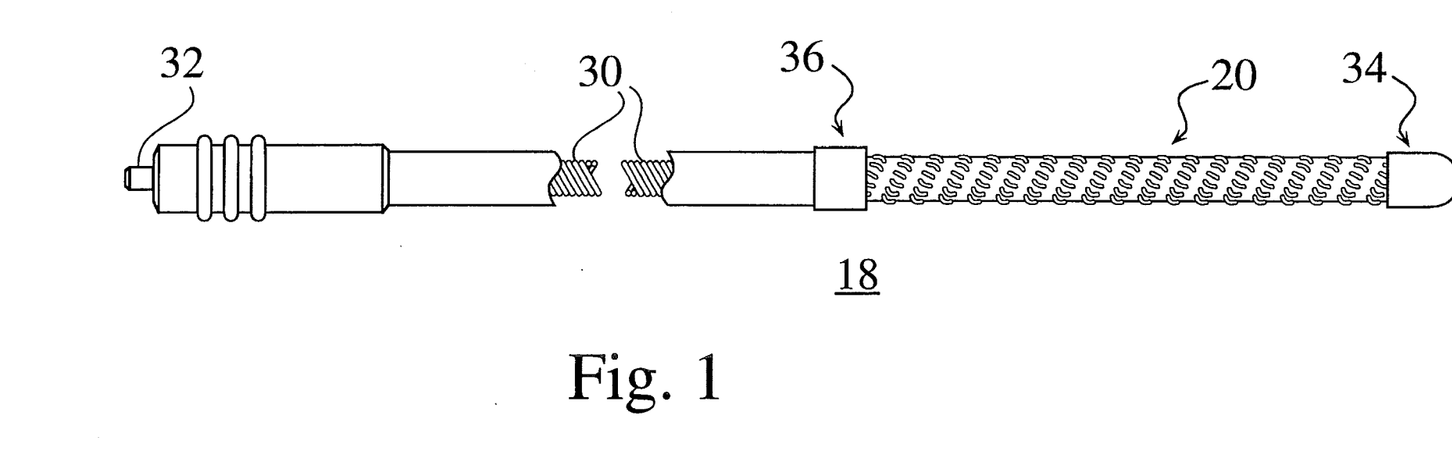
FIG. 1 illustrates a defibrillation electrode.

FIG. 1 shows a lead 18 having an electrode 20 electrically connected to a conductor coil 30 in two locations. The first connection 34 is at the distal end of electrode 20, and the second connection 36 is at the proximal end. These connections can be welds, crimps, and the like, in any combination. The conductor coil 30 is in turn electrically connected to connector 32 for coupling with a pulse generator such as the type described in U.S. Patent No. 5,007,422 to Pless et al., which is assigned to the assignee of the present application. The lead body diameter is generally about 2.5 to 4.5 mm. The lead is disclosed in U.S. patent application Ser. No., 08/126,629, filed 1993 by Mar et al. for a "Flexible Defibrillation Electrode of Improved Construction" which is assigned to the assignee of the present application.

Figure 2:
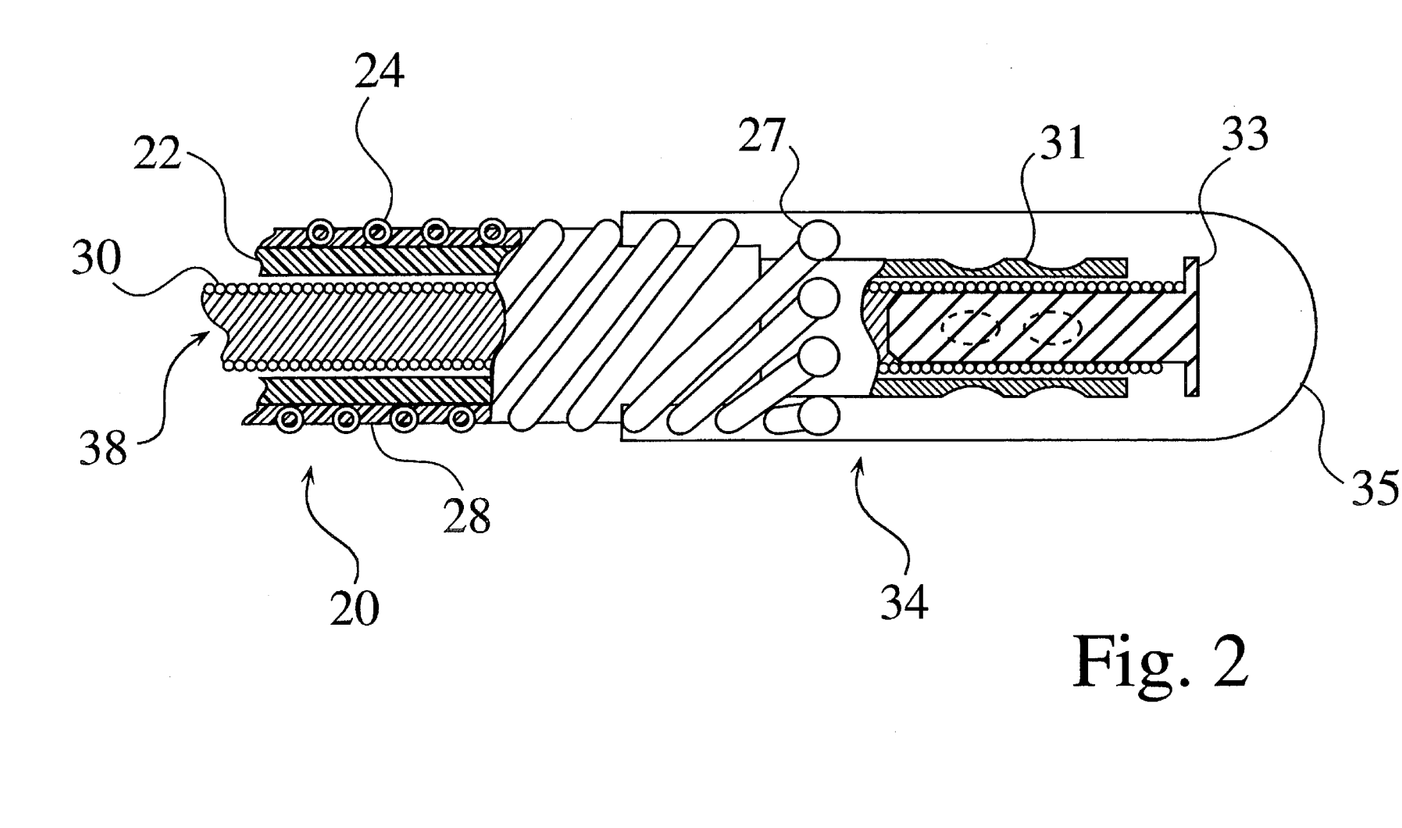
FIG. 2 is a detail view, partially cut away and partially in section, of the distal connection of the lead of FIG. 1.

FIG. 2 shows a detail view of the distal connection of the lead 18 of FIG. 1. Electrode 20 is shown to be constructed of many (six) electrode coils 24 helically wound around a flexible tubular supporting core 22, which may be either electrically conductive or insulative, and may be extruded or molded. This structure has elastomeric material 28, which also may be conductive or insulative, partially encapsulating the electrode coils. The many electrode coils increase conductivity and redundancy. One method of achieving this structure is to completely encapsulate the wrapped electrode coils, then abrade away the surface to partially expose the coils using the method of Mar et al., U.S. Pat. No. 5,226,260, which is assigned to the assignee of the present application and which is incorporated herein by reference. A conductor 30 extends through the lumen of core 22, making connection 34 at the distal end of electrode 20. Conductor 30 is crimped to a sleeve 31 and to a pin 33. In accordance with this invention, the distal ends of electrode coils 24 are melted into balls 27, which are then welded to sleeve 31, forming an electrical connection to the conductor coil. The connection 34 is then covered by a protective cap 35, which may be electrically conductive or insulative. Protective cap 35 seals the electrode connection from body fluids. Conductor coil 30 forms an inner lumen 38 through which a stylet may be placed to stiffen the lead during implantation. Pin 33 serves both as a support for coil 30 and sleeve 31 for crimping, and as a stop for the stylet.

Figure 3:
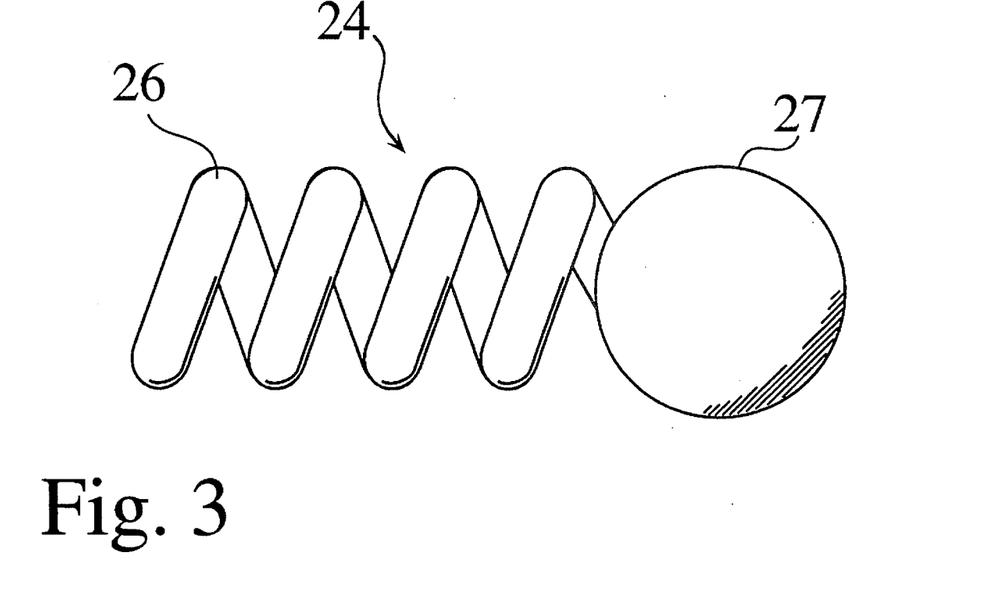
FIG. 3 is a detail view of the distal end of the electrode coil of FIG. 1.

FIG. 3 shows that each electrode coil 24 is made from a helically wound metal wire 26, which may be round or flat in cross section. This wire must be very strong, fatigue resistant, conductive, corrosion resistant, and biocompatible. Platinum iridium is one example of such a material. Electrode coil 24 is shown without an inner core; however, a thin wire or plastic filament could be located within coil 24 to provide either increased electrical conductivity, mechanical redundancy, or both. The filament could be metal or nylon, for example. In order for the lead to be sufficiently thin to be transvenously implantable, electrode coils 24 should be between about 0.2 and 0.4 mm, and wire 26 should be about 0.05 to 0.10 mm in diameter. Close winding of wire 26 into electrode coils 24 provides more exposed metal for charge transfer to tissue. However, space winding decreases the lengths of wire in the coils, decreasing end to end electrode resistance. Additionally, space winding provides more surface for matrix material to mechanically stabilize coils and allows for a substantial volume of matrix material that can flex with the heart and body motion instead of pulling away from the coils. Therefore, a certain amount of space is preferred, typically one-half to one wire diameter space between wires. Similarly, electrode coils 24 can be close or space wound onto core 22. The same general principles apply.

The distal end of each electrode coil 24 is melted into a ball 27, which provides more volume of material to form a strong and reliable crimp or weld. This melted ball structure works particularly well when made of a noble material such as a platinum iridium alloy. A hydrogen torch, also called a "water welder", is one suitable means for melting the coil to form the ball. This device dissociates water into hydrogen and oxygen, then burns the hydrogen to form water again. This process burns cleanly, without incorporating byproducts into the melting coil, which is important for maintaining biocompatibility and material consistency for any subsequent welding.

Figure 4:
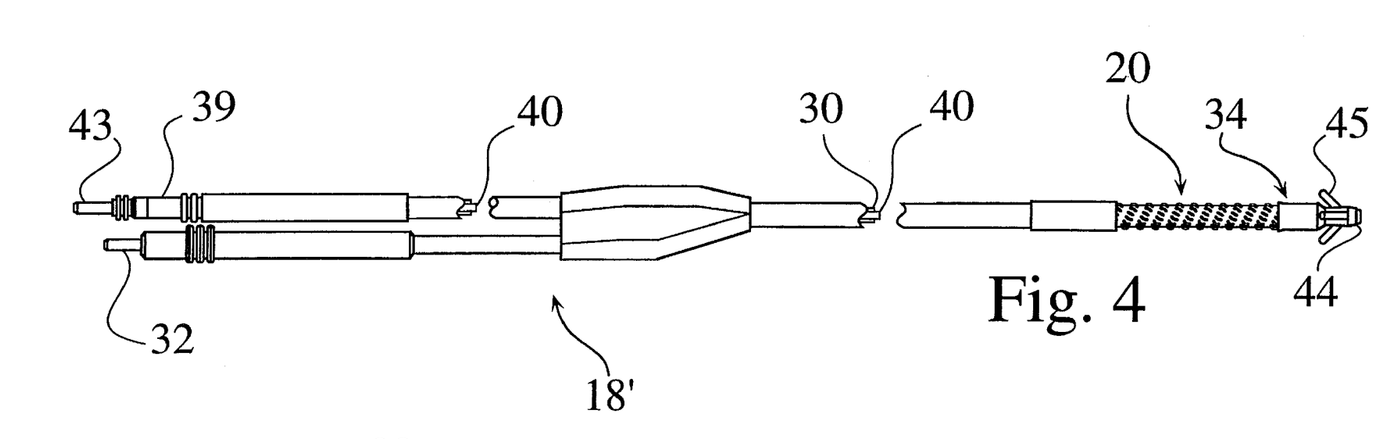
FIG. 4 illustrates an alternative embodiment of the invention which includes a pacing electrode, and uses the electrode for both defibrillation and sensing.

FIG. 4 shows a lead 18' with a pacing electrode 44, and electrode 20 which is used alternately for defibrillation and for sensing. Pacing electrode 44 may be of any of the numerous constructions known in the art. A fixation mechanism 45 is shown as tines, but may be any known in the art, including a screw used for both pacing and fixation. Pacing electrode 44 is electrically connected to a pacing conductor coil 40, which is in turn connected to a pacing connector 43. Electrode 20 is electrically connected to conductor coil 30, which is in turn electrically connected to both defibrillation connector 32 and a sensing connector ring 39.

Figure 5:
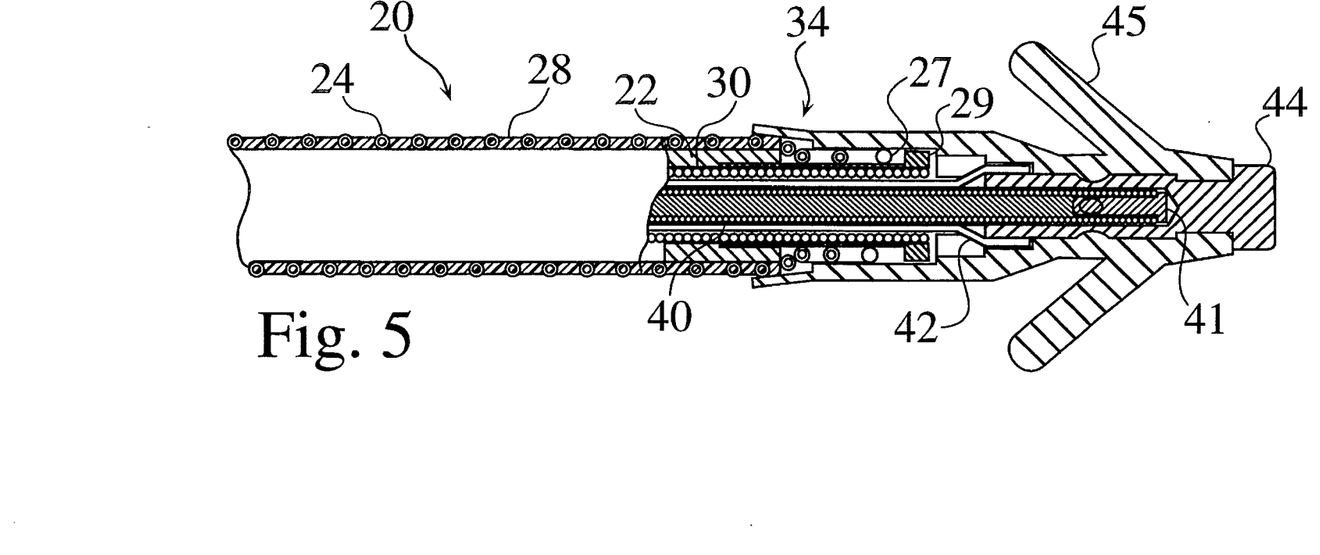
FIG. 5 shows a sectional view of the distal end of the lead of FIG. 4.

FIG. 5 shows a detail view of the distal end of the lead of FIG. 4. Electrode 20 is shown to be constructed of a plurality of electrode coils 24 helically wound around flexible tubular supporting core 22. This structure has elastomeric material 28 partially encapsulating the electrode coils. Conductor 30 extends through the lumen of core 22, making connection 34 at the distal end of electrode 20. Conductor 30 is welded to the face of sleeve 29, as described in U.S. Pat. No. 5,385,578 to Bush et al., for an "Electrical Connection for Medical Electrical Stimulation Electrodes" which is assigned to the assignee of the present application and which is incorporated herein by reference. The distal ends of electrode coils 24 are melted into balls 27, and are then welded to sleeve 29, forming electrical connection 34 to the conductor coil. A pacing conductor coil 40 extends through the lumen of tubular core 22 and is electrically insulated from conductor coil 30 by an insulator 42. Pacing conductor coil 40 is shown connected by a crimp connection to pacing electrode 44 and a crimp pin 41; this connection may alternatively be a weld.

Figure 6:
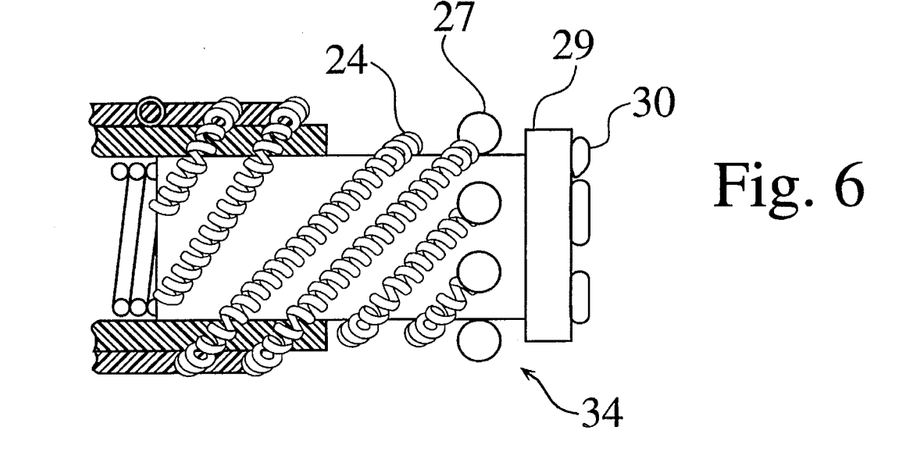
FIG. 6 shows a detail view of the electrical connection of the lead of FIG. 4.

FIG. 6 shows a detail view of electrical connection 34. The distal end of conductor coil 30 has been welded to the face of sleeve 29. Electrode coils 24 have had their distal ends melted into balls 27, then welded to the outside surface of sleeve 29. Alternatively, the balls 27 could have been connected directly to the conductor coil 30.

Figure 7:
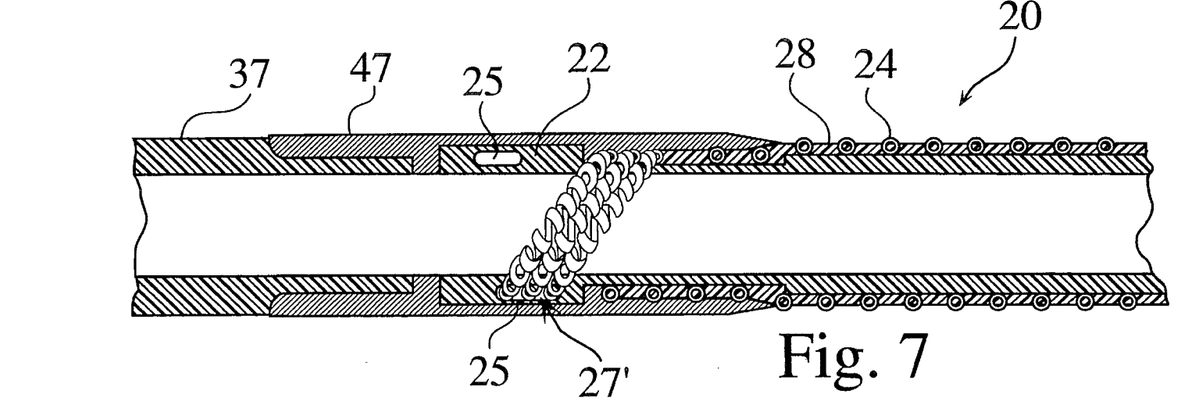
FIG. 7 shows a cross sectional view of the proximal end of the electrode of FIG. 4.

FIG. 7 shows a cross sectional view of the proximal end of electrode 20. Two groups of electrode coils 24 have their proximal ends melted into balls 27' to provide electrical redundancy. Molded electrode core tube 22 has two pockets 25 in its proximal end into which balls 27' are placed prior to wrapping electrode coils 24 onto tube 22. After elastomeric material 28 is applied, an electrical insulation 37 is joined to electrode 20 using a joining material 47, for example silicone rubber. A mandrel is used to keep the lumen open during this process, so that the conductor can be passed through the joint and connected at the distal end of electrode 20.

Figure 8:
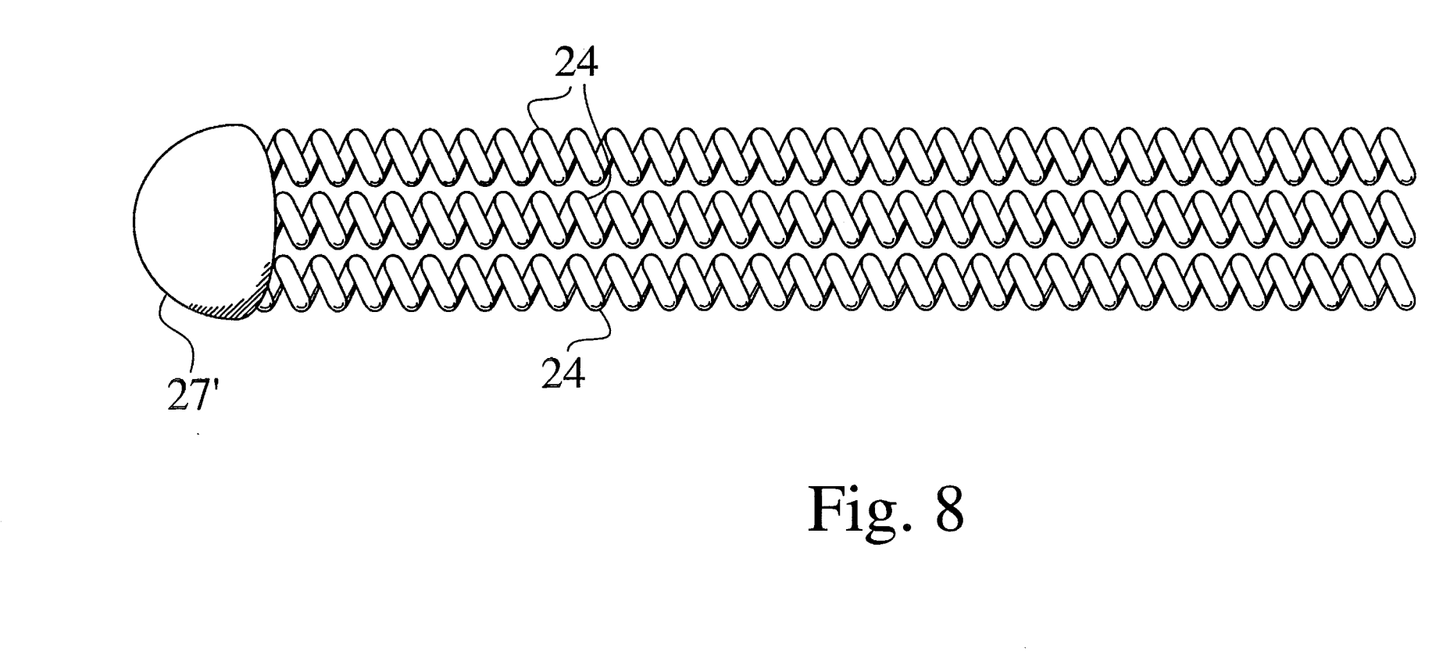
FIG. 8 illustrates one step in the manufacture of the lead of FIG. 4.

FIG. 8 shows one group of three electrode coils 24 with proximal ends melted into ball 27'. This group of three electrode coils can be wound onto a tube such as core tube 22 of FIG. 7 in several ways. The preferred method is to insert a mandrel into a molded core tube, place the mandrel into a lathe-type coil winder, insert one group of three electrode coils 24 into each of two pockets of the tube, then use the coil winder to wind the electrode coils 24 around the tube. After the electrode coils 24 are wound onto the core tube, elastomeric material may be compression molded over the coils and core. An alternative method is to embed electrode coils 24 into uncured elastomeric material that has been rolled into thin strips, then wrap the coil embedded strips of elastomeric material around a core tube, then cure the elastomeric material. A third alternative is to apply uncured elastomeric material to a cured core, then wind electrode coils 24 about the core, embedding them into the elastomeric material. Yet a fourth alternative is to manufacture the core and elastomeric material portion simultaneously by putting uncured rubber onto a mandrel to form both portions; electrode coils 24 are then embedded into the surface of the rubber, and the rubber is cured.

Figure 9:
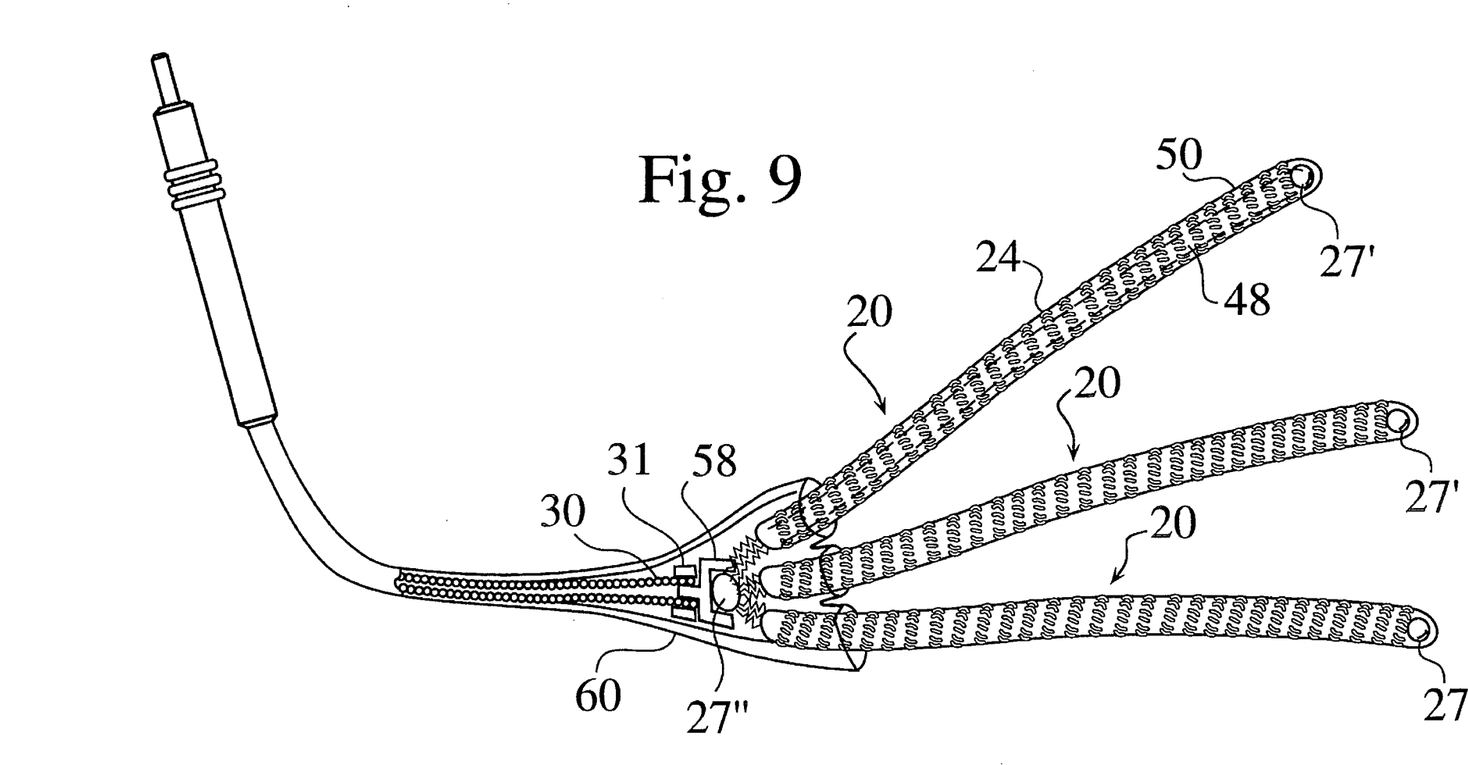
FIG. 9 shows a detail view of an electrode connection of a lead with several electrodes in parallel for subcutaneous implantation.

FIG. 9 illustrates a lead with three electrodes 20, intended for implantation subcutaneously on the left lateral part of the chest. They are of the same polarity, and are connected to a common node on conductor 30. Electrode coils 24 are connected at distal ends by melted balls 27' and wound onto flexible cores 48. Flexible embedding material 50 partially covers electrode coils 24. The proximal ends of electrode coils 24 are all connected by melting them into ball 27". Ball 27" is crimped into metal joining piece 58. Also crimped to metal joining piece 58 is crimp sleeve 31 and conductor coil 30. A protective strain relief molding 60 encapsulates the entire connection.

Figure 10:
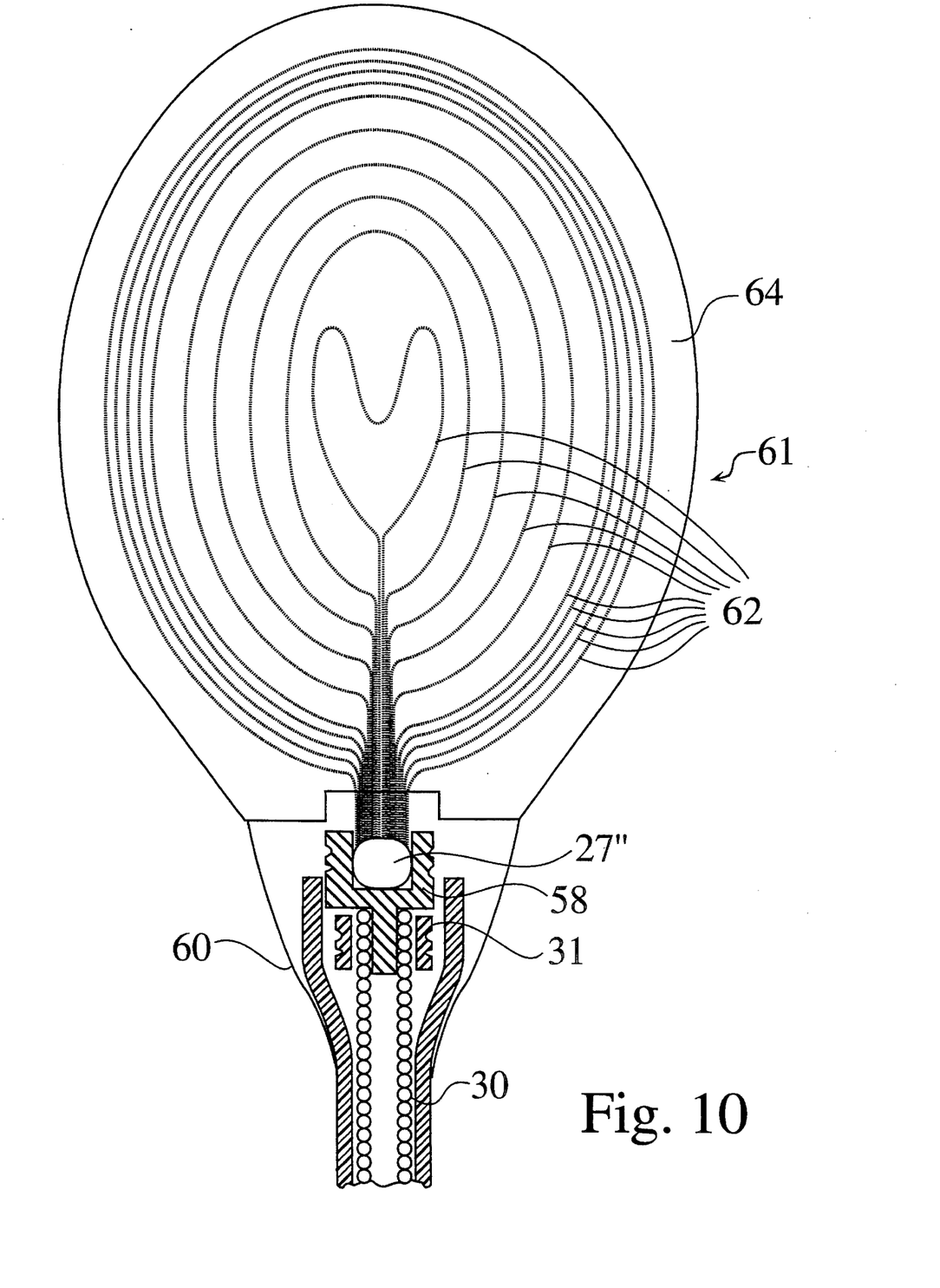
FIG. 10 shows a patch electrode for epicardial or subcutaneous placement.

FIG. 10 illustrates a lead with one patch electrode 61, having a plurality of electrode coils 62 partially embedded in a silicone rubber surface 64. The electrode coils are of the same polarity, and are connected to a common node on conductor 30. Electrode coils 62 are connected by melting both ends of all of them into ball 27". Ball 27" is crimped into metal joining piece 58. Also crimped to metal joining piece 58 is crimp sleeve 31 and conductor coil 30. Alternatively, ball 27" could have been connected directly to conductor 30. A protective strain relief molding 60 encapsulates the entire connection.

Because the electrode coil wire is longer and thinner than the electrode elements of the prior art, the electrode of the present invention can be made with a certain amount of resistance along its length, say, 3 to 15 ohms. This property of the electrode can be used to direct defibrillation energy to selected regions of the heart by careful choice of connection locations of electrode to conductor. For example, if the electrode 20 of FIG. 4 were placed with its distal end in the apex of the RV, current would be steered to the RV apex since that is where the conductor attaches to the electrode at connection 34. On the other hand, because of the electrode connections 34 and 36 on either end of electrode 20 of FIG. 1, the current distribution would be more even along the electrode length than in the electrode of FIG. 4, since the potential is the same at either end, assuming a very low resistance conductor 30. In this case, the end to end electrode resistance is also reduced, with the highest resistance being in the middle of the electrode. The connection could also be made in the middle of the electrode, instead of or in addition to the ends. With the electrode connected to the conductor in only the middle of the electrode and not the ends, current density would be more even since end effects would be reduced. Several connections between the conductor and the electrode may be made along the length of one electrode. This is desirable for reducing overall resistance, particularly when the electrode is long.

The above has been offered for illustrative purposes only and is not intended to limit the scope of the invention of this application, which is as defined in the claims below.

That which is claimed is:

1. A method of electrically connecting a coil having a diameter to a conductor comprising the steps of:

melting back an end of said coil to form a ball of larger diameter than said coil diameter:

crimping or welding said conductor to a metal joining piece; and crimping or welding said ball to said metal joining piece.

2. The method of claim 1 in which a water welder is used to melt the end of said coil.

3. The method of claim 1 in which said coil is platinum iridium.

4. A method of electrically connecting at least two coiled wires comprising the steps of:

holding at least one end of each of said at least two coiled wires substantially parallel to each other and close together; and melting back said at least one end of each of said at least two coiled wires into a ball of metal such that each of said coiled wires is attached to said ball.

5. The method of claim 4 in which a water welder is used to melt the end of said coiled wires.

6. A method of joining at least two coiled wires to a conductor, comprising the steps of:

holding at least one end of each of said at least two coiled wires substantially parallel to each other and close together;

melting back said at least one end of each of said at least two coiled wires into a ball of metal such that each of said coiled wires is attached to said ball;

crimping or welding a joining piece to said conductor; and crimping or welding said ball to said joining piece.

7. The method of claim 6 in which a water welder is used to melt the end of said coiled wires.

8. The method of claim 6 wherein said step of holding at least one end of each of said at least two coiled wires substantially parallel to each other and close together comprises holding both ends of each of said at least two coiled wires substantially parallel to each other and close together, and wherein said step of melting back said at least one end of each of said at least two coiled wires into a ball of metal such that each of said coiled wires is attached to said ball comprises melting back both ends of each of said at least two coiled wires into a ball of metal such that each of said coiled wires is electrically and mechanically attached to said ball at both ends.

9. A method of joining at least two coiled wires to a conductor, comprising the steps of:

holding at least one end of each of said at least two coiled wires substantially parallel to each other and close together;

melting back said at least one end of each of said at least two coiled wires into a ball of metal such that each of said coils is attached to said ball; and connecting said ball to said conductor.

10. The method of claim 9 in which said coiled wires are platinum iridium.

11. A method of electrically connecting a wire having a diameter of about 0.05 to 0.10 mm to a conductor, comprising the steps of:

winding said wire into a coil having a diameter of about 0.2 to 0.4 mm;

melting back an end of said wire to form a ball of larger diameter than said wire; and connecting said ball to said conductor.

12. The method of claim 11, and further including the step of encapsulating said connected ball with a protective molding.

* * * * *